United States Patent [19]

Weisz et al.

[11] 4,098,339
[45] Jul. 4, 1978

[54] UTILIZATION OF LOW BTU NATURAL GAS

[75] Inventors: Paul B. Weisz, Yardley, Pa.; John C. Zahner, Princeton, N.J.

[73] Assignee: Mobil Oil Corporation, New York, N.Y.

[21] Appl. No.: 731,613

[22] Filed: Oct. 13, 1976

Related U.S. Application Data

[63] Continuation-in-part of Ser. No. 698,449, Jun. 21, 1976, abandoned.

[51] Int. Cl.$^2$ .............................................. E21B 43/16
[52] U.S. Cl. ............................ 166/305 R; 48/196 A; 48/214 A; 252/373; 260/449.5
[58] Field of Search ............ 48/196 A, 196 R, 214 A, 48/197 R, 206; 252/373; 260/449.5, 449.6; 166/274, 256, 266, 305 R

[56] References Cited

U.S. PATENT DOCUMENTS

| | | | |
|---|---|---|---|
| 2,684,975 | 7/1954 | Frye | 260/449.6 |
| 3,387,942 | 6/1968 | Habermehl et al. | 252/373 |
| 3,442,332 | 5/1969 | Keith | 166/266 |
| 3,763,205 | 10/1973 | Green | 260/449.5 |

Primary Examiner—S. Leon Bashore
Assistant Examiner—George C. Yeung
Attorney, Agent, or Firm—Charles A. Huggett; Ronald J. Cier

[57] ABSTRACT

Natural gas of low heating value, high $CO_2$ content, is converted to valuable products by the combination process of steam reforming the desulfurized gas, subjecting the effluent of the steam reformer to a water gas shift reaction and converting the resultant carbon dioxide, the unreacted carbon monoxide and hydrogen to liquid product useful as fuel, e.g. methanol. In a preferred embodiment, the gas phase separated from the liquid fuel products is processed to provide a gas sufficiently rich in carbon dioxide for use in tertiary recovery of petroleum from natural reservoirs which have produced the quantity of oil available by natural drive.

5 Claims, 1 Drawing Figure

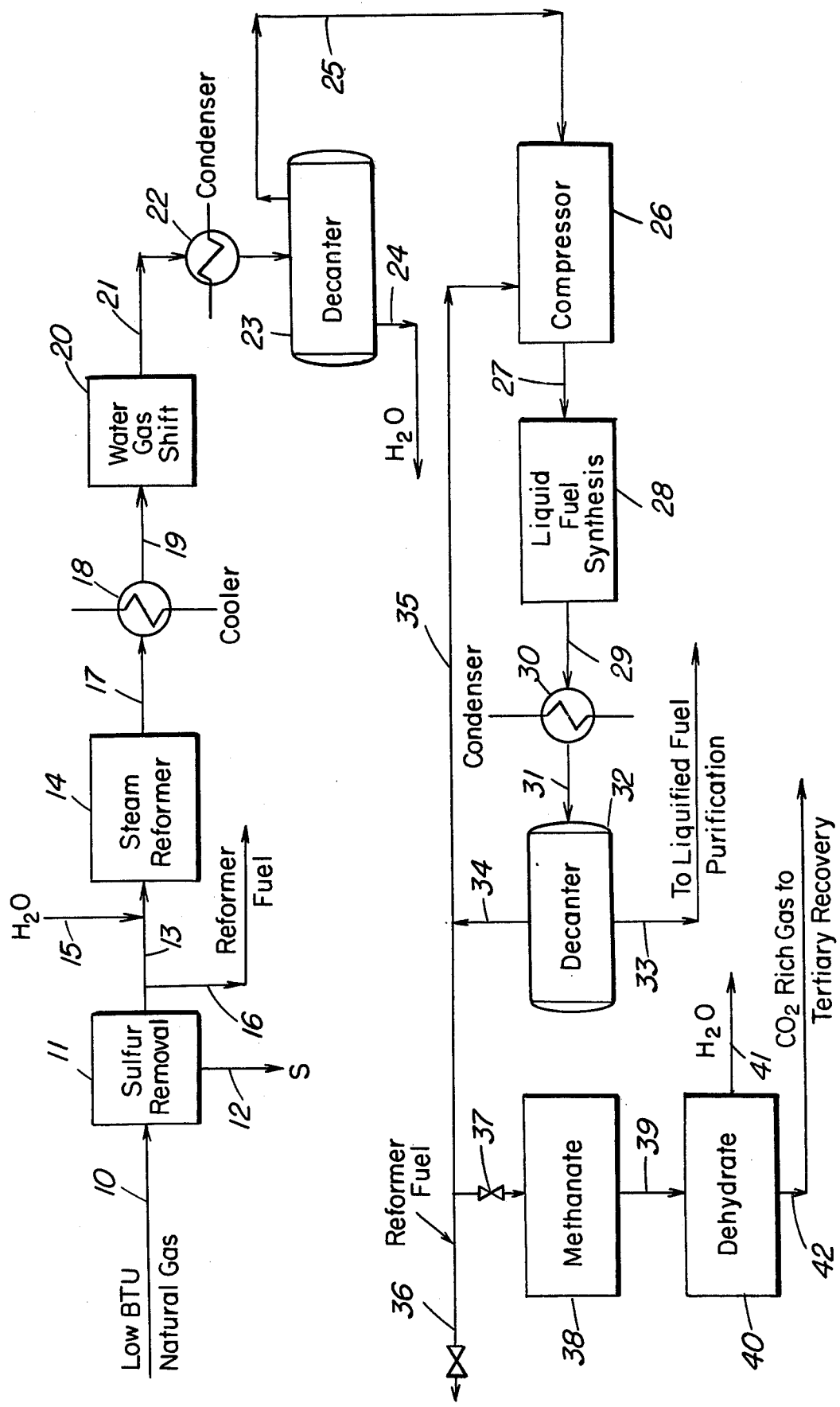

UTILIZATION OF LOW BTU NATURAL GAS

CROSS-REFERENCE TO RELATED APPLICATION

This application is a continuation-in-part of copending application Ser. No. 698,449, filed June 21, 1976 and now abandoned.

FIELD OF THE INVENTION

This invention relates to production of liquid fuel in a manner for utilization of natural gas which has a low heating value (low BTU content) by reason of relatively high concentration of carbon dioxide in admixture with the methane fuel contained therein. Natural gas adaptable to use in the process will contain about 50% or more, by volume, of carbon dioxide. In its preferred embodiment, the invention is also concerned with supply of a product gas rich in carbon dioxide and having a reduced methane content as compared with the natural gas processed. Such product gas is utilized in tertiary recovery of liquid petroleum from underground reservoirs which have been depleted to the extent possible by primary recovery operations.

BACKGROUND OF THE INVENTION

In providing a combination of process steps which yield valuable products from natural gas heretofore considered valueless, the invention utilizes known technology for (1) generating a synthesis gas of carbon monoxide and hydrogen from reaction of methane and water; (2) generating carbon dioxide and hydrogen by the water gas shift reaction of carbon monoxide with water; (3) synthesis of methanol or liquid hydrocarbons by reaction of carbon monoxide and hydrogen; and (4) tertiary recovery of petroleum by injection to a spent underground reservoir of carbon dioxide which contains little methane, it being known that methane reduces solubility of carbon dioxide in petroleum.

The natural gases of interest in the process of this invention have been heretofore regarded as having no significant commercial value. Natural gas containing mixtures of carbon dioxide and methane in about equal volumes and those still richer in methane have been processed to separate methane from carbon dioxide and thus provide fuel gas of pipe line quality. However, it has been considered uneconomic to produce natural gas from extensive known reservoirs in which the gas contains 75% by volume, more or less, of carbon dioxide. The cost for separation of the methane content is too great in comparison with value of the recovered methane to support construction and operation of separation facilities. Assuming a use for the carbon dioxide in tertiary recovery at petroleum reservoirs within a distance which can justify piping the gas, these mixtures are unsuitable because of their content of methane which is known to inhibit solubility of carbon dioxide in petroleum.

For a great number of years, natural gas had been considered to be the proper natural source material for generation of synthesis gas containing carbon monoxide and hydrogen to be used in synthesis of methanol, for synthesis of hydrocarbons by the well-known Fischer-Tropsch reaction, or the like. As the cost of natural gas has risen, more attention is being given to the vast deposits of coal in the United States and elsewhere as a source of synthesis gas.

SUMMARY OF THE INVENTION

This invention provides a technique for commercially practicable utilization of the hitherto valueless natural gases containing upwards of fifty volume percent of carbon dioxide by a combination of steps which convert the carbon content of the methane and a portion of the carbon content as carbon dioxide into carbon monoxide admixed with hydrogen. The resultant mixture is subjected to a synthesis reaction for generation of such liquid fuels as methanol or hydrocarbons, thus enriching the gas with respect to carbon dioxide. A portion of that off-gas is recycled to the synthesis step and a portion is withdrawn as purge which may be utilized as fuel. In a preferred alternative, the purge gas is reacted to convert its carbon monoxide component to methane. The resultant gas, rich in carbon dioxide, is sufficiently poor in methane for use in tertiary recovery operations.

BRIEF DESCRIPTION OF DRAWING

A flow sheet of a typical process configuration according to the invention is illustrated in the single FIGURE of the annexed drawing.

SPECIFIC EMBODIMENTS OF THE INVENTION

As shown in the drawing, a stream of low BTU gas, produced from conventional wells, is supplied by line 10. Such a gas may contain 75% carbon dioxide and 25% methane by volume, usually admixed with a small amount of sulfur compounds primarily hydrogen sulfide. Such sulfur, if present, is preferably first removed at an absorber 11 by any of the known techniques for sorption in liquids or on solid bodies without major reduction in carbon dioxide content. This step may be accomplished by the Selexol process described by Valentine at pages 60–62 of the Oil and Gas Journal for Nov. 18, 1974. Alternatively, sulfur may be removed by sorption on activated charcoal followed by zinc oxide. Sulfur compounds withdrawn by line 12 are passed to suitable sulfur recovery stages, such as a Claus plant, not shown.

The mixture of carbon dioxide and methane, now reduced to less than 1 ppm sulfur, is passed by line 13 to steam reformer 14 where it is reacted with water from line 15. A portion of the desulfurized gas may be withdrawn by line 16 to serve as fuel for steam reformer 14. The steam reformer is operated under conventional conditions to convert the methane and water to carbon monoxide and hydrogen. Many of the catalysts for this purpose will promote reaction of a portion of the carbon dioxide with hydrogen so generated to produce carbon monoxide and water.

Typical of steam reformer operations are temperatures of 1200° to 1850° F at pressures in the range of 200 to 600 pounds per square inch, absolute (psia). A suitable catalyst is nickel oxide on a refractory support such as alumina. For making methanol the optimal feed for a steam reformer is 25% carbon dioxide, 75% methane to yield a hydrogen to carbon monoxide product ratio of 2/1. It will be seen that the present feed varies widely from the ideal. In general, it is preferred to supply excess water to the reformer to protect the catalyst against coking. For the present purpose, it is suitable to provide a molar ratio of water to methane of about 1.2 to 2.4.

The reaction product from reformer 14 passes by line 17 to cooler 18 where the mixture is reduced to a temperature suited to the water gas shift reaction. The cooled mixture leaving cooler 18 passes by line 19 to water gas shift reactor 20 which is loaded with a suitable catalyst for promotion of the water gas shift reaction of carbon monoxide and water to yield carbon dioxide and hydrogen. Pressure in reactor 20 will be approximately the same as exit pressure of the steam reformer 14, reduced by the pressure drop through the equipment. The higher the pressure in reactor 20, the more water is needed to protect the catalyst against coking. Additional water, if required, may be added by injection (not shown) to line 19).

The temperature in reactor 20 will be chosen to suit the type of catalyst employed. With a catalyst such as chrome promoted iron, the operation is conducted at 650°–900° F. An alternate is copper oxide and zinc oxide on a refractory support, e.g. alumina, operating at 400°–500° F.

The product gas leaving reactor 20 will have a hydrogen to carbon monoxide ratio suitable to the liquid fuel synthesis to follow. Note that this stream may be enriched with carbon monoxide, if necessary, by passing a portion of the stream from line 19 around reactor 20 to blend with reactor 20 effluent in line 21 by which the mixture passes to condenser 22. Water condensed in condenser 22 is decanted in decanter 23 and removed by line 24, from which it may be recycled for use in the process or discharged from the system.

The gas phase from decanter 23 is transferred by line 25 to compressor 26, which may be of the multi-stage type with inter-stage cooling. Note that some water vapor in the effluent of decanter 23 may condense at inter-stage cooling. Such condensate is preferably discharged for recycle or other disposition. The gaseous mixture, primarily carbon monoxide, hydrogen and carbon dioxide, is compressed to a high pressure suitable to the synthesis reaction and passed by line 27 to liquid fuel synthesis reactor 28 for reaction of carbon monoxide with hydrogen to produce methanol, hydrocarbons or the like by known techniques for reduction of carbon monoxide. For example, methanol synthesis may be conducted at temperatures in the neighborhood of 500° F and pressures of 1000–2500 psia over a catalyst of copper and zinc oxides an alumina. The Fischer-Tropsch synthesis is will known to reduce carbon monoxide with hydrogen to hydrocarbons over potassium promoted iron catalyst. Newer techniques involve the use of carbon monoxide reduction in combination with a porous crystalline alumino-silicate such as zeolite ZSM-5.

The carbon monoxide reduction reaction is highly exothermic and requires extraction of heat to maintain suitable reaction temperatures. One technique for achieving this result is introduction of cold reactant at spaced points along the path of reactants. For purposes of the present invention, it is preferred to dispose the catalyst in tubes within a vessel for generation of steam from water about the exterior of the tubes. This permits close control of temperatures and permits two stages of reaction, with the second stage at a lower temperature by permitting steam to evolve at a lower pressure from the second stage vessel and thus promote completion of the reaction.

Effluent of reactor 28 at line 29 is largely depleted of carbon monoxide content and passes to condenser 30 for condensation of the liquid fuel product. From condenser 30, the product stream passes by line 31 to decanter 32 from which the liquid fuel product is withdrawn by line 33 for distillation and such other finishing steps as may be appropriate.

The gas phase from decanter 32 is withdrawn at line 34 and recycled in part by line 35 to compressor 26 for conversion of carbon monoxide content thereof in reactor 28. It will be necessary to withdraw a portion of the gas phase from the system to maintain the level of inert substances, such as nitrogen, methane and carbon dioxide, at an acceptable level. It is preferred that this purge stream be processed to make a carbon dioxide stream of sufficiently high purity for use in tertiary recovery and for other uses. In the event such uses are not economically attractive because of location of the plant or other reason, the purge stream from line 34 may be burned for its fuel value by discharge at valved line 36.

For manufacture of carbon dioxide rich gas, say about 90% by volume or higher, the purge gas passes through valved line 37 to a methanation reactor 38 to convert the carbon monoxide content to methane. The methanation product passes by line 39 to dehydrator 40 for removal of residual water, as by sorption on alumina. The dried product is available for use in tertiary recovery by techniques long known in the production art. See U.S. Pat. No. 2,623,596, Whorton et al., Dec. 30, 1952.

A typical operation according to the invention is set forth in the Example below, based on computer calculations simulating the several reactions at equilibrium conditions. It will be recognized that any specific plant may vary somewhat from these results, depending largely on kinetic considerations.

EXAMPLE

The natural gas processed by computer simulation was that found in a field in Texas. Analysis of the gas is 75% carbon dioxide, 25% methane with 50–500 ppm hydrogen sulfide. After desulfurization to nil hydrogen sulfide, the mixture of methane and carbon dioxide is reacted with water over nickel oxide on alumina at 1560° F and 200 psia. The composition of feed and product are shown in Table 1.

Product of that steam reforming step is cooled and passed over chrome promoted iron catalyst for water gas shift adjusted to provide an exit temperature held below 770° F. The composition of the product is set out in Table 1.

TABLE 1

| | Composition of Feed and Products in Sequential Steam Reforming and Water Gas Shift | | |
|---|---|---|---|
| | Feed Gas Mols | Reformer Product, Mols | Shift Reactor Product, Mols |
| $H_2$ | | 158.55 | 246.34 |
| $CO$ | | 211.71 | 123.42 |
| $CO_2$ | 300 | 180.85 | 269.14 |
| $H_2O$ | 120 | 146.58 | 58.29 |
| $CH_4$ | 100 | 7.43 | 7.43 |

The product from the shift reaction is then converted to methanol at 500° F. and 1480 psia over copper and zinc oxides on alumina at a recycle ratio of 3.3082 volumes of gas effluent from decanter 32 per volume of fresh feed to the methanol synthesis reactor. Utilization of synthesis gas is 77.607% at a conversion per pass of 31.943%. Composition of streams is shown in Table 2 in mols. For convenience the reference numeral of the drawing at which each stream is found is noted in parenthesis on each column of the Table.

TABLE 2

| | Composition of Streams at Methanol Synthesis Reactor | | | | | |
|---|---|---|---|---|---|---|
| | Fresh Feed (25) | Liquid Product (33) | Purge (36,37) | Recycle (35) | Combined Feed (27) | Reactor Exit (29) |
| CO | 123.42 | 0.37 | 45.43 | 304.04 | 427.46 | 349.84 |
| $CO_2$ | 269.14 | 18.77 | 231.46 | 1548.98 | 1818.12 | 1799.21 |
| $H_2$ | 246.84 | 0.18 | 34.70 | 232.24 | 479.08 | 267.12 |
| $H_2O$ | 0.00 | 18.87 | 0.04 | 0.27 | 0.27 | 19.18 |
| $CH_3OH$ | 0.00 | 95.78 | 0.74 | 4.96 | 4.96 | 101.48 |
| $CH_4$ | 7.43 | 0.06 | 7.37 | 49.35 | 56.78 | 56.78 |

In the preferred embodiment, a "Purge" stream such as shown in Table 3 resulting from different processing conditions shown in Tables 1 and 2 is reacted at 500° F and at the pressure of the synthesis reaction in contact with nickel oxide on alumina catalyst to react hydrogen and carbon monoxide to methane and water. The product after dehydration contains 6.83 mols carbon monoxide, 211.11 mols carbon dioxide, nil mols hydrogen, and 14.66 mols methane. It will be seen that the methane content compared to the natural gas has been drastically reduced, providing a gas suitable for tertiary recovery operations. A reasonable estimate of value of the residual gas for tertiary recovery is represented by one volume of additional crude petroleum for each volume of methanol produced.

It will be recognized that this methanation reaction is the reverse of that conducted in the steam reformer 14. The reaction is reversible and equilibrium is shifted by variations in the conditions of reaction. For example, increased pressure favors reaction to methane with decreased number of mols of gas according to the equation:

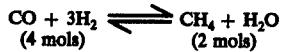

$$CO + 3H_2 \rightleftharpoons CH_4 + H_2O$$
$$(4 \text{ mols}) \qquad (2 \text{ mols})$$

TABLE 3

| | Enriching $CO_2$ Content of Purge Gas | |
|---|---|---|
| | Purge (37) | $CO_2$ Rich Gas (42) |
| CO | 16.12 | 6.83 |
| $CO_2$ | 211.11 | 211.11 |
| $H_2$ | 27.88 | — |
| $H_2O$ | .03 | — |
| $CH_3OH$ | .26 | — |
| $CH_4$ | 5.37 | 14.66 |

We claim:

1. A process for economic utilization of natural gas having low heating value by reason of containing carbon dioxide in admixture with the methane content thereof, which process comprises subjecting a natural gas having substantial methane content in admixture with at least fifty volume percent of carbon dioxide based on total volume of said gas to the following steps in the sequence recited:

(a) mixing said gas with water and reacting the mixture in contact with a catalyst to promote the reforming reaction of methane and water to produce carbon monoxide and hydrogen under temperature and pressure conditions conducive of said reforming reaction;

(b) reacting the product of step (a) in contact with a catalyst to promote the water gas shift reaction of a portion of the carbon monoxide with water to produce carbon dioxide and hydrogen under temperature and pressure conditions conducive of said shift reaction; and (c) reacting the product of step (b), in contact with a carbon monoxide reduction catalyst for promotion of synthesis reaction between carbon dioxide, the unreacted carbon monoxide and hydrogen, to produce methanol or hydrocarbons, which are liquid at normal temperature of 70° F and atmospheric pressure, under conditions of temperature and pressure conducive of said synthesis reaction thereby producing as the product of said synthesis reaction a mixture comprising:

(1) said methanol or hydrocarbons which are liquid at normal temperature of 70° F and atmospheric pressure, and (2) a gaseous by-product enriched in carbon dioxide as compared with said natural gas.

2. The process of claim 1 wherein said gaseous by-product enriched in carbon dioxide as compared with said natural gas is injected into a subterranean oil bearing formation to enhance production of oil therefrom.

3. The process of claim 2 wherein said gaseous by-product is reacted in contact with a catalyst for promotion of methanation reaction between carbon monoxide and hydrogen, when present in said gaseous by-product to produce methane and water under conditions of temperature and pressure conducive of said methanation reaction before injection as aforesaid.

4. The process of claim 3 wherein the product of said methanation reaction is dehydrated before injection as aforesaid.

5. The process of claim 1 wherein sulfur-containing compounds, present in said natural gas, are substantially removed therefrom prior to subjecting said natural gas to said reforming reaction of step (a).

* * * * *